(12) United States Patent
Metzger et al.

(10) Patent No.: US 7,780,672 B2
(45) Date of Patent: Aug. 24, 2010

(54) FEMORAL ADJUSTMENT DEVICE AND ASSOCIATED METHOD

(75) Inventors: Robert Metzger, Wakarusa, IN (US); Radu Serban, Warsaw, IN (US); Thomas K. Donaldson, Redlands, CA (US)

(73) Assignee: Biomet Manufacturing Corp., Warsaw, IN (US)

( * ) Notice: Subject to any disclaimer, the term of this patent is extended or adjusted under 35 U.S.C. 154(b) by 624 days.

(21) Appl. No.: 11/363,548

(22) Filed: Feb. 27, 2006

(65) Prior Publication Data

US 2007/0233140 A1 Oct. 4, 2007

(51) Int. Cl.
- A61B 17/15 (2006.01)
- A61B 17/56 (2006.01)
- A61B 17/58 (2006.01)
- A61B 17/90 (2006.01)

(52) U.S. Cl. .................. 606/88; 606/86 R; 606/87; 606/89

(58) Field of Classification Search .................. 606/88, 606/79–89, 96, 98, 99, 102
See application file for complete search history.

(56) References Cited

U.S. PATENT DOCUMENTS

| | | | |
|---|---|---|---|
| 1,763,730 A | 6/1930 | Von Lackum |
| 1,959,615 A | 5/1934 | Derrah |
| 2,433,815 A | 12/1947 | LaForge |
| 2,455,655 A | 12/1948 | Carroll |
| 2,702,550 A | 2/1955 | Rowe |
| 2,724,326 A | 11/1955 | Long |
| 2,955,530 A | 10/1960 | Nilo |
| 3,048,522 A | 8/1962 | Velley |
| 3,229,006 A | 1/1966 | Nohl |
| 3,514,791 A | 6/1970 | Sparks |
| 3,554,197 A | 1/1971 | Dobbie et al. |
| 3,624,747 A | 11/1971 | McKnight et al. |
| 3,631,596 A | 1/1972 | Glaus et al. |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,807,393 A | 4/1974 | McDonald |
| 3,811,449 A | 5/1974 | Gravlee et al. |

(Continued)

FOREIGN PATENT DOCUMENTS

CH 117960 5/1927

(Continued)

OTHER PUBLICATIONS

"Hand Instruments", High Performance, Precision Series brochure by Arthrotek, copyright 2000.

(Continued)

Primary Examiner—Thomas C Barrett
Assistant Examiner—Sameh Boles
(74) Attorney, Agent, or Firm—Harness, Dickey

(57) ABSTRACT

A femoral adjustment device to balance a flexion gap. The device includes a body attachable to a distal femur, the body having a cutting guide and an adjustment mechanism operable to balance the flexion gap, wherein upon balancing the flexion gap, the cutting guide is operable to guide at least one cut in the distal femur.

12 Claims, 8 Drawing Sheets

U.S. PATENT DOCUMENTS

| | | |
|---|---|---|
| 3,869,731 A | 3/1975 | Waugh et al. |
| 3,903,549 A | 9/1975 | Deyerle |
| 3,905,105 A | 9/1975 | Tuke et al. |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,299,224 A | 11/1981 | Noiles |
| 4,304,178 A | 12/1981 | Haberle et al. |
| 4,311,145 A | 1/1982 | Esty et al. |
| 4,344,193 A | 8/1982 | Kenny |
| 4,349,018 A | 9/1982 | Chambers |
| 4,373,709 A | 2/1983 | Whitt |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| D273,895 S | 5/1984 | Kenna |
| D274,091 S | 5/1984 | Kenna |
| 4,453,421 A | 6/1984 | Umano et al. |
| 4,501,269 A | 2/1985 | Bagby |
| 4,509,518 A | 4/1985 | McGarry et al. |
| 4,516,276 A | 5/1985 | Mittelmeier et al. |
| 4,534,365 A | 8/1985 | Bonetta et al. |
| 4,545,375 A | 10/1985 | Cline |
| 4,554,686 A | 11/1985 | Baker |
| 4,562,598 A | 1/1986 | Kranz et al. |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,624,254 A | 11/1986 | McGarry et al. |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,678,470 A | 7/1987 | Nashef et al. |
| 4,682,598 A | 7/1987 | Beraha |
| 4,685,460 A | 8/1987 | Thornton |
| 4,703,751 A * | 11/1987 | Pohl .......................... 606/62 |
| 4,711,233 A | 12/1987 | Brown |
| 4,718,413 A | 1/1988 | Johnson |
| 4,718,916 A | 1/1988 | Morscher et al. |
| 4,739,751 A | 4/1988 | Sapega et al. |
| 4,794,854 A | 1/1989 | Swaim |
| 4,817,602 A | 4/1989 | Beraha |
| 4,834,757 A | 5/1989 | Brantigan |
| 4,838,891 A | 6/1989 | Branemark et al. |
| 4,863,472 A | 9/1989 | Tormala et al. |
| 4,888,022 A | 12/1989 | Huebsch |
| 4,911,721 A | 3/1990 | Branemark et al. |
| 4,935,023 A | 6/1990 | Whiteside et al. |
| 4,936,852 A | 6/1990 | Kent et al. |
| 4,950,296 A | 8/1990 | McIntyre |
| 4,952,213 A | 8/1990 | Bowman et al. |
| 4,961,740 A | 10/1990 | Ray et al. |
| 4,961,954 A | 10/1990 | Goldberg et al. |
| 4,964,865 A | 10/1990 | Burkhead et al. |
| 4,979,949 A | 12/1990 | Matsen, III et al. |
| 4,979,957 A | 12/1990 | Hodorek |
| 4,985,038 A | 1/1991 | Lyell |
| 5,007,912 A | 4/1991 | Albrektsson et al. |
| 5,015,247 A | 5/1991 | Michelson |
| 5,032,132 A | 7/1991 | Matsen, III et al. |
| 5,035,700 A | 7/1991 | Kenna |
| 5,060,678 A | 10/1991 | Bauman et al. |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert et al. |
| 5,092,869 A | 3/1992 | Waldron |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,441 A | 4/1992 | McDowell |
| 5,111,987 A | 5/1992 | Moeinzadeh et al. |
| 5,122,144 A | 6/1992 | Bert et al. |
| 5,123,906 A | 6/1992 | Kelman |
| 5,129,909 A | 7/1992 | Sutherland |
| 5,147,365 A | 9/1992 | Whitlock et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden et al. |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,702 A | 1/1993 | Bales et al. |
| 5,178,622 A | 1/1993 | Lehner, II |
| 5,183,053 A | 2/1993 | Yeh et al. |
| 5,183,464 A | 2/1993 | Dubrul et al. |
| 5,186,178 A | 2/1993 | Yeh et al. |
| 5,192,327 A | 3/1993 | Brantigan |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Mikhail |
| 5,228,459 A | 7/1993 | Caspari et al. |
| 5,234,433 A | 8/1993 | Bert et al. |
| 5,258,004 A | 11/1993 | Bales et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| D343,247 S | 1/1994 | Walen |
| 5,275,166 A | 1/1994 | Vaitekunas et al. |
| 5,275,603 A | 1/1994 | Ferrante et al. |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,322,505 A | 6/1994 | Krause et al. |
| 5,329,845 A | 7/1994 | Bichel |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Lyell |
| 5,364,402 A | 11/1994 | Mumme et al. |
| 5,368,599 A | 11/1994 | Hirsch et al. |
| 5,379,133 A | 1/1995 | Kirk |

| | | | | | |
|---|---|---|---|---|---|
| 5,382,249 A | 1/1995 | Fletcher | 5,755,803 A | 5/1998 | Haines et al. |
| 5,383,937 A | 1/1995 | Mikhail | 5,769,855 A | 6/1998 | Bertin et al. |
| 5,390,683 A | 2/1995 | Pisharodi | 5,769,899 A | 6/1998 | Schwartz et al. |
| 5,395,376 A | 3/1995 | Caspari et al. | 5,772,594 A | 6/1998 | Barrick |
| D358,647 S | 5/1995 | Cohen et al. | 5,788,700 A | 8/1998 | Morawa et al. |
| 5,423,827 A | 6/1995 | Mumme et al. | 5,810,827 A | 9/1998 | Haines et al. |
| 5,425,355 A | 6/1995 | Kulick | 5,810,831 A | 9/1998 | D'Antonio |
| 5,425,745 A | 6/1995 | Green et al. | 5,817,109 A | 10/1998 | McGarry et al. |
| 5,443,475 A | 8/1995 | Auerbach et al. | 5,842,477 A | 12/1998 | Naughton et al. |
| 5,445,639 A | 8/1995 | Kuslich et al. | 5,846,931 A | 12/1998 | Hattersley et al. |
| 5,445,642 A | 8/1995 | McNulty et al. | 5,860,980 A | 1/1999 | Axelson, Jr. et al. |
| 5,454,365 A | 10/1995 | Bonutti | 5,860,981 A | 1/1999 | Bertin et al. |
| 5,454,815 A | 10/1995 | Geisser et al. | 5,866,415 A | 2/1999 | Villeneuve |
| 5,454,816 A | 10/1995 | Ashby | 5,871,493 A | 2/1999 | Sjostrom et al. |
| 5,456,268 A | 10/1995 | Bonutti | 5,879,354 A | 3/1999 | Haines et al. |
| 5,472,415 A | 12/1995 | King et al. | 5,888,219 A | 3/1999 | Bonutti |
| 5,484,095 A | 1/1996 | Green et al. | 5,899,914 A | 5/1999 | Zirps et al. |
| 5,486,178 A | 1/1996 | Hodge | 5,908,424 A | 6/1999 | Bertin et al. |
| 5,490,854 A | 2/1996 | Fisher et al. | 5,911,723 A | 6/1999 | Ashby et al. |
| 5,497,933 A | 3/1996 | DeFonzo et al. | 5,913,874 A | 6/1999 | Berns et al. |
| 5,507,763 A | 4/1996 | Petersen et al. | 5,916,219 A | 6/1999 | Matsuno et al. |
| 5,514,139 A | 5/1996 | Goldstein et al. | 5,921,990 A | 7/1999 | Webb |
| 5,514,143 A | 5/1996 | Bonutti et al. | 5,925,049 A | 7/1999 | Gustilo et al. |
| 5,520,692 A | 5/1996 | Ferrante | 5,961,499 A | 10/1999 | Bonutti et al. |
| 5,520,694 A | 5/1996 | Dance et al. | 5,997,566 A | 12/1999 | Tobin |
| 5,522,897 A | 6/1996 | King et al. | 6,007,537 A | 12/1999 | Burkinshaw et al. |
| 5,540,695 A | 7/1996 | Levy | 6,012,456 A | 1/2000 | Schuerch |
| 5,545,222 A | 8/1996 | Bonutti | 6,015,419 A | 1/2000 | Strome et al. |
| 5,546,720 A | 8/1996 | LaBruzza | 6,019,767 A | 2/2000 | Howell |
| 5,549,683 A | 8/1996 | Bonutti | 6,022,350 A | 2/2000 | Ganem et al. |
| 5,554,169 A | 9/1996 | Green et al. | 6,024,746 A | 2/2000 | Katz |
| 5,562,675 A | 10/1996 | McNulty et al. | 6,056,754 A | 5/2000 | Haines et al. |
| 5,569,163 A | 10/1996 | Francis et al. | 6,056,756 A | 5/2000 | Eng et al. |
| 5,569,261 A | 10/1996 | Marik et al. | 6,059,817 A | 5/2000 | Bonutti et al. |
| 5,570,700 A | 11/1996 | Vogeler | 6,059,831 A | 5/2000 | Braslow et al. |
| 5,578,039 A | 11/1996 | Vendrely et al. | 6,063,095 A | 5/2000 | Wang et al. |
| 5,593,448 A | 1/1997 | Dong | 6,077,270 A | 6/2000 | Katz |
| 5,597,379 A | 1/1997 | Haines et al. | 6,077,287 A | 6/2000 | Taylor et al. |
| 5,608,052 A | 3/1997 | Zmitek et al. | 6,086,593 A | 7/2000 | Bonutti |
| 5,609,603 A | 3/1997 | Linden | 6,090,122 A | 7/2000 | Sjostrom et al. |
| 5,624,444 A | 4/1997 | Wixon et al. | 6,096,043 A | 8/2000 | Techiera et al. |
| 5,624,463 A | 4/1997 | Stone et al. | 6,099,531 A | 8/2000 | Bonutti |
| 5,632,745 A | 5/1997 | Schwartz | 6,099,532 A | 8/2000 | Florea |
| 5,643,272 A | 7/1997 | Haines et al. | 6,102,850 A | 8/2000 | Wang et al. |
| 5,649,946 A | 7/1997 | Bramlet | 6,106,529 A | 8/2000 | Techiera |
| 5,649,947 A | 7/1997 | Auerbach et al. | 6,118,845 A | 9/2000 | Simon et al. |
| 5,653,714 A | 8/1997 | Dietz et al. | 6,120,509 A | 9/2000 | Wheeler |
| 5,659,947 A | 8/1997 | Eilers et al. | 6,132,472 A | 10/2000 | Bonutti |
| 5,662,656 A | 9/1997 | White | 6,156,070 A | 12/2000 | Incavo et al. |
| 5,662,710 A | 9/1997 | Bonutti | 6,159,246 A | 12/2000 | Mendes et al. |
| 5,667,069 A | 9/1997 | Williams, Jr. | 6,171,340 B1 | 1/2001 | McDowell |
| 5,667,511 A | 9/1997 | Vendrely et al. | 6,174,321 B1 | 1/2001 | Webb |
| 5,667,512 A | 9/1997 | Johnson | 6,185,315 B1 | 2/2001 | Schmucker et al. |
| 5,667,520 A | 9/1997 | Bonutti | 6,187,023 B1 | 2/2001 | Bonutti |
| D385,163 S | 10/1997 | Hutchins et al. | 6,195,158 B1 | 2/2001 | Cadell et al. |
| 5,681,316 A | 10/1997 | DeOrio et al. | 6,197,064 B1 | 3/2001 | Haines et al. |
| 5,683,398 A | 11/1997 | Carls et al. | 6,198,794 B1 | 3/2001 | Peshkin et al. |
| 5,688,279 A | 11/1997 | McNulty et al. | 6,211,976 B1 | 4/2001 | Popovich et al. |
| 5,688,280 A | 11/1997 | Booth, Jr. et al. | 6,214,051 B1 | 4/2001 | Badorf et al. |
| 5,694,693 A | 12/1997 | Hutchins et al. | 6,228,121 B1 | 5/2001 | Khalili |
| 5,702,447 A | 12/1997 | Walch et al. | 6,258,127 B1 | 7/2001 | Schmotzer et al. |
| 5,702,475 A | 12/1997 | Zahedi et al. | 6,277,136 B1 | 8/2001 | Bonutti |
| 5,704,941 A | 1/1998 | Jacober et al. | 6,290,703 B1 | 9/2001 | Ganem et al. |
| 5,707,350 A | 1/1998 | Krause et al. | 6,290,704 B1 | 9/2001 | Burkinshaw et al. |
| 5,712,543 A | 1/1998 | Sjostrom | 6,325,806 B1 | 12/2001 | Fox |
| 5,716,360 A | 2/1998 | Baldwin et al. | 6,328,572 B1 | 12/2001 | Higashida et al. |
| 5,718,708 A | 2/1998 | Webb | 6,338,737 B1 | 1/2002 | Toledano et al. |
| 5,720,752 A | 2/1998 | Elliott et al. | 6,358,266 B1 | 3/2002 | Bonutti |
| 5,723,331 A | 3/1998 | Tubo et al. | 6,361,565 B1 | 3/2002 | Bonutti |
| 5,733,292 A | 3/1998 | Gustilo et al. | 6,391,040 B1 | 5/2002 | Christoudias |
| 5,749,876 A * | 5/1998 | Duvillier et al. ............ 606/88 | 6,406,495 B1 | 6/2002 | Schoch et al. |
| 5,755,731 A | 5/1998 | Grinberg | 6,409,722 B1 | 6/2002 | Hoey et al. |
| 5,755,791 A | 5/1998 | Whitson et al. | 6,423,063 B1 | 7/2002 | Bonutti |

| | | | |
|---|---|---|---|
| 6,431,743 B1 | 8/2002 | Mizutani et al. | |
| D462,767 S | 9/2002 | Meyer et al. | |
| 6,458,135 B1 | 10/2002 | Harwin et al. | |
| 6,468,280 B1 | 10/2002 | Saenger et al. | |
| 6,468,289 B1 | 10/2002 | Bonutti | |
| 6,478,799 B1 | 11/2002 | Williamson | |
| 6,482,209 B1 | 11/2002 | Engh et al. | |
| 6,500,181 B1 | 12/2002 | Portney | |
| 6,503,267 B2 | 1/2003 | Bonutti et al. | |
| 6,554,837 B1 | 4/2003 | Hauri et al. | |
| 6,554,838 B2 | 4/2003 | McGovern et al. | |
| 6,558,391 B2 | 5/2003 | Axelson, Jr. et al. | |
| 6,575,982 B1 | 6/2003 | Bonutti | |
| 6,602,259 B1 | 8/2003 | Masini | |
| 6,620,181 B1 | 9/2003 | Bonutti | |
| 6,632,225 B2 | 10/2003 | Sanford et al. | |
| 6,635,073 B2 | 10/2003 | Bonutti | |
| 6,673,077 B1 | 1/2004 | Katz | |
| 6,676,662 B1 | 1/2004 | Bagga et al. | |
| 6,695,848 B2 | 2/2004 | Haines | |
| 6,702,821 B2 | 3/2004 | Bonutti | |
| 6,770,078 B2 | 8/2004 | Bonutti | |
| 6,979,299 B2 | 12/2005 | Peabody et al. | |
| 7,029,477 B2 * | 4/2006 | Grimm | 606/88 |
| 7,172,599 B2 | 2/2007 | Steffensmeier et al. | |
| 7,261,719 B1 | 8/2007 | Twomey et al. | |
| 2001/0018589 A1 | 8/2001 | Muller | |
| 2001/0034554 A1 | 10/2001 | Pappas | |
| 2001/0037155 A1 | 11/2001 | Merchant | |
| 2002/0029038 A1 | 3/2002 | Haines | |
| 2002/0029045 A1 | 3/2002 | Bonutti | |
| 2002/0052606 A1 | 5/2002 | Bonutti | |
| 2002/0116023 A1 | 8/2002 | Fletcher et al. | |
| 2002/0173797 A1 | 11/2002 | Van Zile et al. | |
| 2002/0198529 A1 | 12/2002 | Masini | |
| 2002/0198531 A1 | 12/2002 | Millard et al. | |
| 2003/0028196 A1 | 2/2003 | Bonutti | |
| 2003/0060831 A1 | 3/2003 | Bonutti | |
| 2003/0100906 A1 | 5/2003 | Rosa et al. | |
| 2003/0100907 A1 | 5/2003 | Rosa et al. | |
| 2003/0130665 A1 | 7/2003 | Pinczewski et al. | |
| 2003/0171757 A1 | 9/2003 | Coon et al. | |
| 2003/0212403 A1 | 11/2003 | Swanson | |
| 2003/0216741 A1 | 11/2003 | Sanford et al. | |
| 2003/0220641 A1 | 11/2003 | Thelen et al. | |
| 2003/0225413 A1 | 12/2003 | Sanford et al. | |
| 2004/0039395 A1 | 2/2004 | Coon et al. | |
| 2004/0102785 A1 | 5/2004 | Hodorek et al. | |
| 2004/0138670 A1 | 7/2004 | Metzger | |
| 2004/0220583 A1 | 11/2004 | Pieczynski et al. | |
| 2005/0049603 A1 * | 3/2005 | Calton et al. | 606/87 |
| 2005/0113840 A1 | 5/2005 | Metzger et al. | |
| 2005/0149042 A1 | 7/2005 | Metzger | |
| 2005/0177170 A1 * | 8/2005 | Fisher et al. | 606/88 |
| 2006/0095049 A1 | 5/2006 | Zannis et al. | |
| 2006/0142774 A1 | 6/2006 | Metzger | |
| 2006/0142778 A1 | 6/2006 | Dees | |
| 2007/0083209 A1 | 4/2007 | Schenberger et al. | |
| 2007/0282451 A1 | 12/2007 | Metzger et al. | |

FOREIGN PATENT DOCUMENTS

| | | |
|---|---|---|
| DE | 337437 | 5/1921 |
| FR | 1111677 | 3/1956 |
| WO | WO-96/07361 | 3/1996 |
| WO | WO-9729703 | 8/1997 |

OTHER PUBLICATIONS

"AGC 3000 Intramedullary Surgical Technique Using PMMA Fixation," 1987, Biomet, Inc.

"AGC Distal Fem Cutter for Dr. Hardy," Biomet, Inc., Jun. 22, 1989.

"AGC Total Knee System, Intramedullary Without Distractor Surgical Technique," 1989, Biomet, Inc.

"ACG Traditional Surgical overview", copyright 2001 Biomet Orthopedics, Inc.

"AGC-S Total Knee System, Surgical Technique for the AGC-S Total Knee System," 1992, Biomet, Inc.

"Anatomic Axial Alignment Instrumentation," 1994, Biomet, Inc.

"The AGC Revision Knee System Surgical Technique," 1997 Biomet, Inc.

AGC Total Knee System, Unicondylar Surgical Overview, Biomet, Inc. (4 pages).

Genus, brochure entitled "Uni Knee System," Biomet, Inc., Nov. 15, 1998.

Insall/Burstein II Modular Knee System by Zimmer, Inc. copyright 1989.

Keys, Graham W., "Reduced Invasive Approach for Oxford II Medial Unicompartmental Knee Replacement—a Preliminary Study," The Knee, (1999) pp. 193-196.

Microplasty™ minimally invasive knee instruments brochure, Surgical Technique for the Maxim®, Ascent™ and Vanguard™ Total Knee Systems. Biomet Orthopedics, Inc., Feb. 29, 2004.

MIS Minimally Invasive Solution—The M/G Unicompartmental Knee by Zimmer, 4 sheets.

MIS Minimally Invasive Solution The M/G Unicompartmental Knee Minimally Invasive Surgical Technique, by Zimmer, copyright 2000 (pp. 1-27).

Nex Gen Complete Knee Solution-Intramedually Instrumentation Surgical Technique-For the NexGen Cruciate Retaining & Legacy Posterior Stabilized Knee-Publication date unknown, but before Aug. 1, 2001.

NexGen Complete Knee Solution-Extramedullary/Intramedullary Tibial Resector Surgical Technique-Publication date unknown, but before Aug. 1, 2001.

NexGen Complete Knee Solution-Multi-Reference 4-in-1 Femoral Instrumentation-Anterior Reference Surgical Technique-Publication date unknown, but before Aug. 1, 2001.

NexGen Complete Knee Solution-Surgical Technique for the LPS-Flex Fixed Bearing Knee-Publication date unknown, but before Aug. 1, 2001.

NexGen System Complete Knee Solution—Design Rationale—publication date unknown.

Orthopaedic Update, No. 18, The Fudger™—The Ultimate Weapon in the Femoral Referencing War, Biomet, Inc. (2 pages).

Scorpio! Single Axis Total Knee System—Passport Total Knee Instruments—Passport A.R. Surgical Technique by Sryker Howmedica Osteonics, Copyright 2000.

Simple Instruments Surgical Technique for the Knee, copyright 2000 Biomet, Inc.

Surgical Navigation for Total Knee Arthroplasty-Believed to have been presented at the American Academy of Orthopedic Surgeons in Feb. 2001.

The Oxford, brochure entitled "Unicompartmental Knee System", Biomet Orthopedics, Inc., Jul. 15, 2004.

* cited by examiner

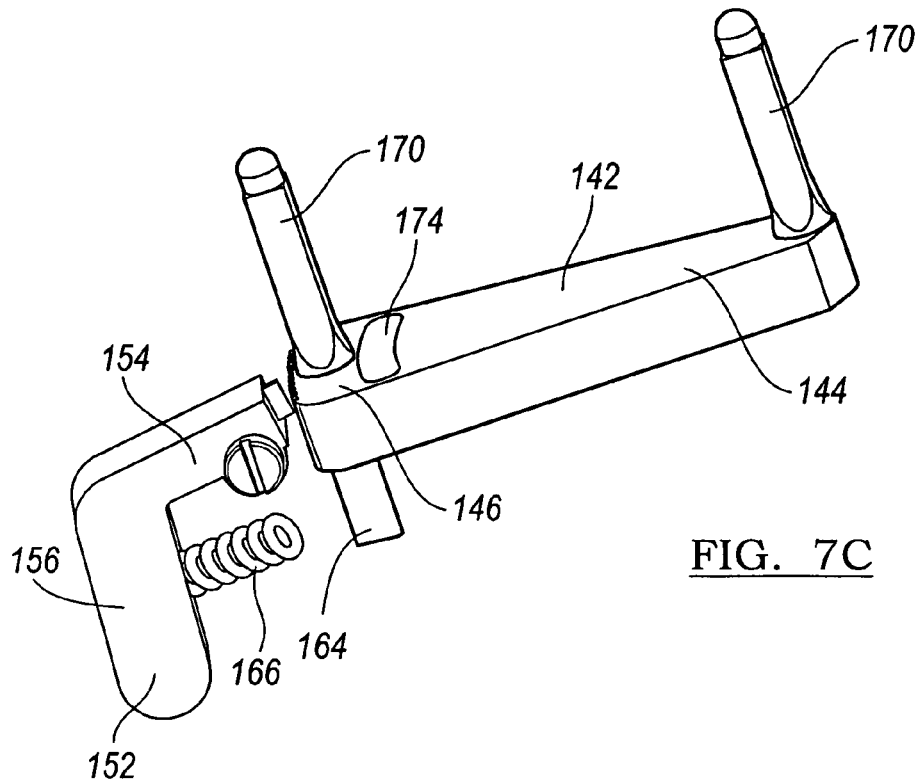
FIG. 7C
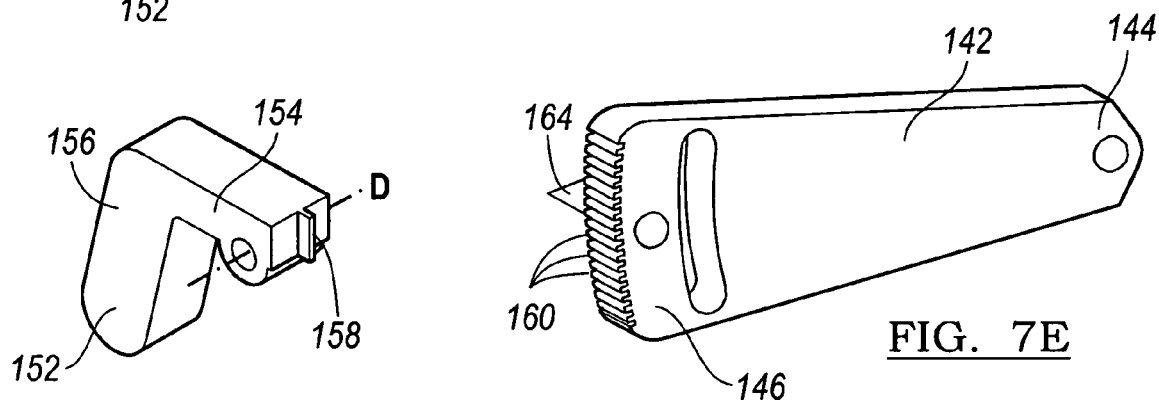
FIG. 7D
FIG. 7E
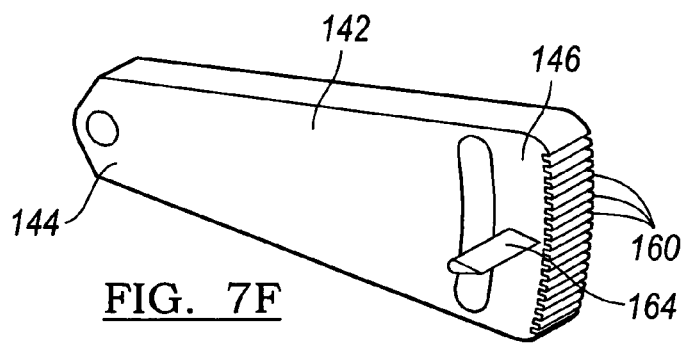
FIG. 7F

FEMORAL ADJUSTMENT DEVICE AND ASSOCIATED METHOD

INTRODUCTION

Various devices, such as joint distraction instruments, are used to balance the flexion gap in knee arthroplasty. Too small flexion gap may reduce mobility, while too large flexion gap can produce instability.

Although the existing devices can be satisfactory for their intended purposes, there is still a need for femoral adjustment devices and associated methods for balancing the flexion gap and performing femoral cuts.

SUMMARY

The present teachings provide a femoral adjustment device to balance a flexion gap. The device includes a body attachable to a distal femur, the body having a cutting guide and an adjustment mechanism operable to balance the flexion gap, wherein upon balancing the flexion gap, the cutting guide is operable to guide at least one cut in the distal femur.

The present teachings also provide a method for balancing a flexion gap in a knee procedure. The method includes attaching a cutting guide to a distal femur, adjusting the cutting guide selectively in at least of one of a linear adjustment in an antero-posterior direction relative to a distal femur and a rotational adjustment relative to the distal femur, until the flexion gap is balanced, and guiding a cut.

The present teachings further provide a method for balancing a flexion gap in a knee procedure. The method includes flexing the knee, attaching a cutting block device to a distal femur, balancing the flexion gap using the cutting block device, and guiding a cut with the cutting block device.

The present teaching further provide a femoral adjustment system to balance a flexion gap, the system comprising a body attachable to a distal femur, the body having a drilling guide and an adjustment mechanism operable to balance the flexion gap, wherein upon balancing the flexion gap, the drilling guide is operable to guide drilling at least one hole in the distal femur, and a spacer block positioned in the flexion gap.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 7A-F illustrate various perspective views of components of a rotational adjustment mechanism according to the present teachings;

DESCRIPTION OF VARIOUS ASPECTS

The following description is merely exemplary in nature and is in no way intended to limit the invention, its application, or uses. For example, although the present teachings are illustrated for applications in balancing the flexion gap in knee surgery, the present teachings can be used for other cut adjustments.

Figure 1:
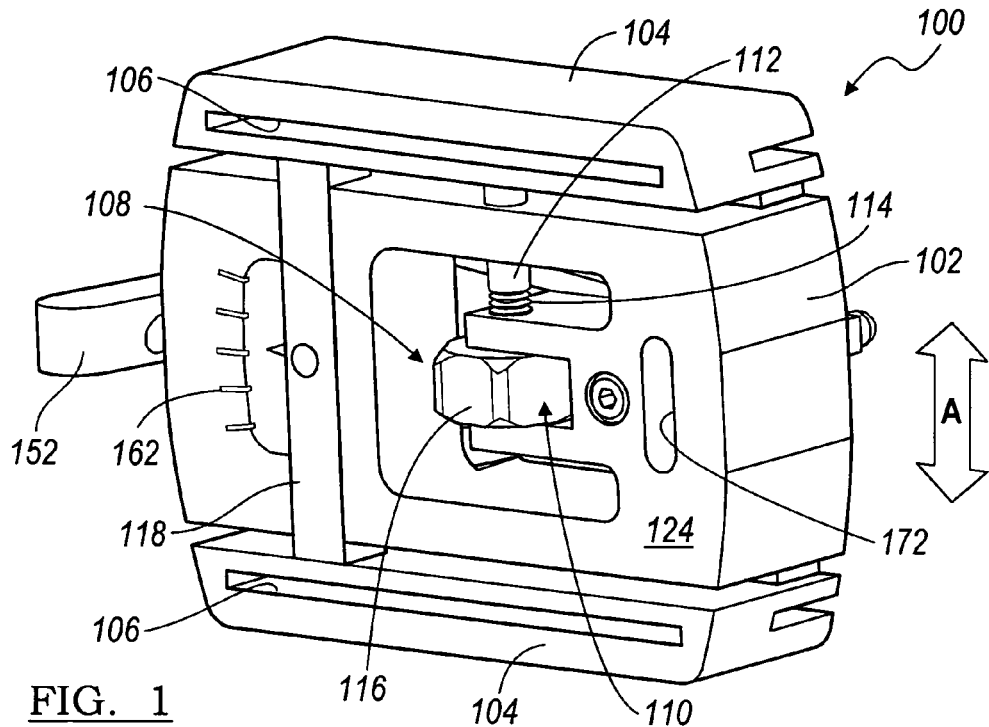
FIG. 1 is a front isometric view of a femoral adjustment device according to the present teachings.
Figure 1A:
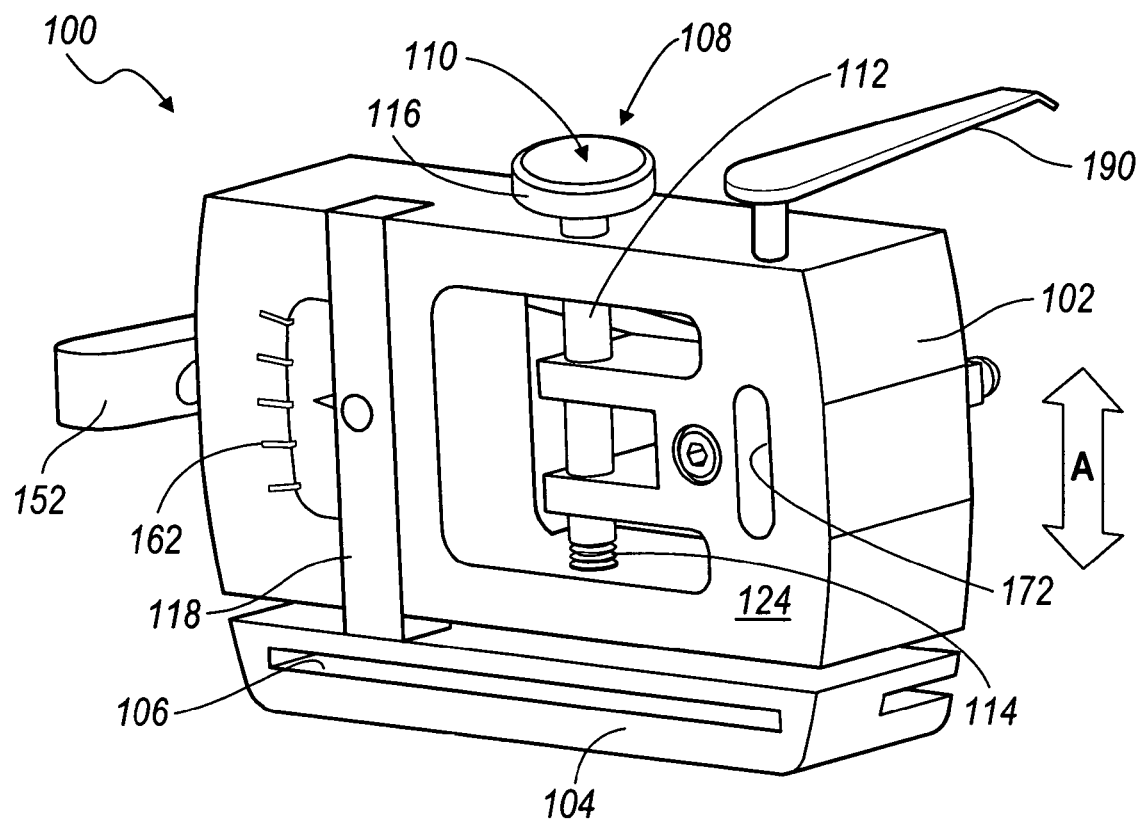
FIG. 1A is a front isometric view of a femoral adjustment device according to the present teachings.
Figure 9:
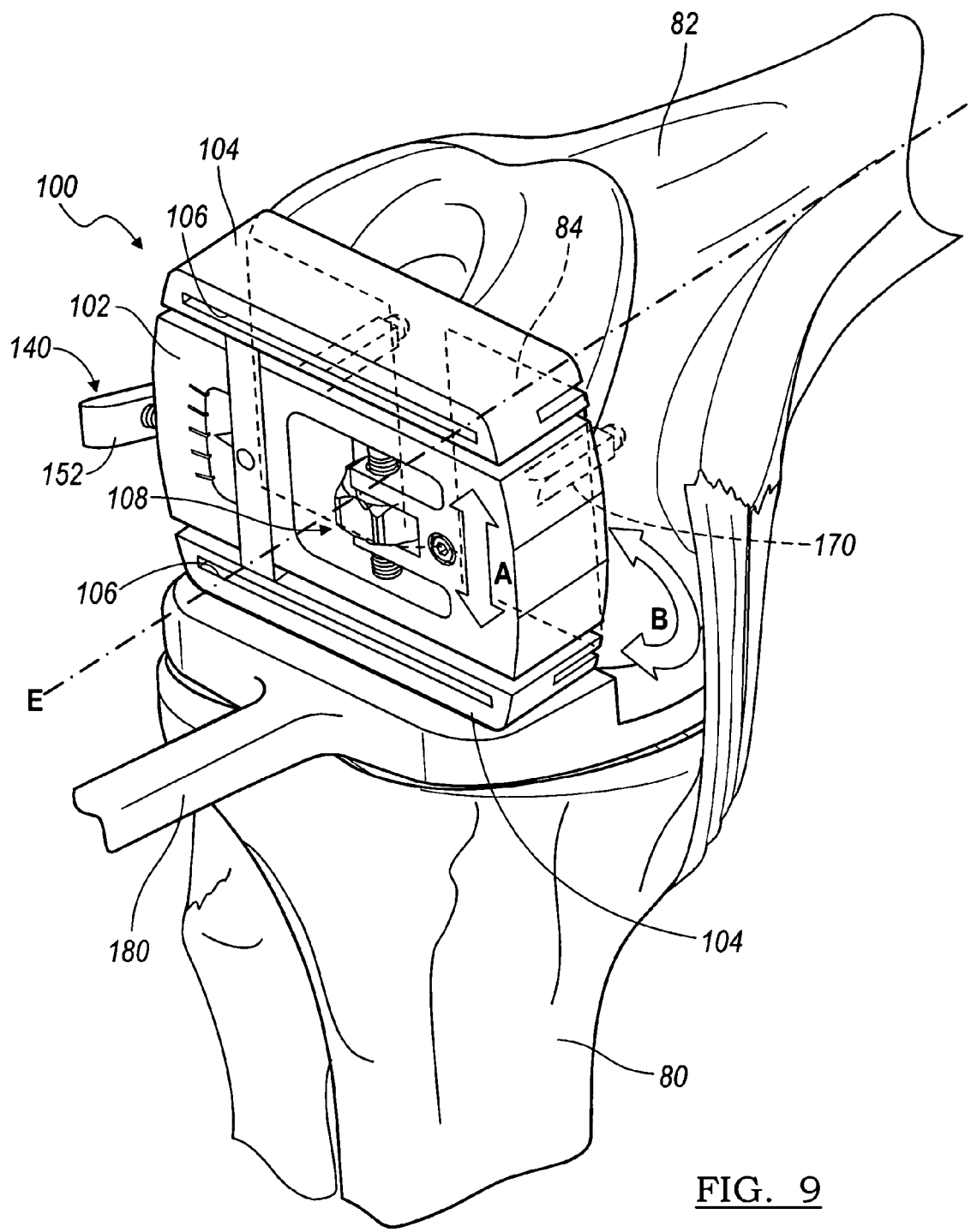
FIG. 9 illustrates a method for balancing a flexion gap using a femoral adjustment device according to the present teachings.

Referring to FIG. 1, an exemplary femoral adjustment/cutting block device 100 according to the present teachings can include a body 102 attachable to a resected surface 84 of a distal femur 82, as shown in FIG. 9, and at least one cutting member 104 coupled to the body 102 and defining a cutting guide 106, such as, for example, a slot, or an edge or other appropriate guide for cutting with a saw blade or other cutting instrument. Two cutting members 104 are illustrated in FIG. 1 and are disposed on opposite sides of the body 102 such that the femoral adjustment device 100 can be used selectively to make, for example, posterior cuts for the distal femur 82 of the left or right knee by an appropriate 180-degree rigid body rotation. It will be appreciated, however, that the femoral adjustment device 100 can also be used to make anterior, posterior, chamfer and other cuts in either the right or the left knee, as determined by the surgeon, and by appropriate rigid body rotations and relative adjustments. FIG. 1A illustrates an exemplary femoral adjustment device 100 having only one cutting member 104. Further, the cutting guide 106 can be defined directly in the body 102.

The femoral adjustment device 100 can also include a linear adjustment mechanism 108 for adjusting a linear displacement of the cutting guide 106 relative to the resected surface 84 of the distal femur 82 in a direction substantially perpendicular to the cutting guide 106, as indicated by a double arrow "A", and corresponding to the antero-posterior (A/P) direction. The linear adjustment mechanism 108 can include a linear actuator 110 for incrementally displacing the cutting guide 106 relative to the body 102 in the direction defined by the linear displacement. The linear actuator 110 can include a knob or nut 116 threadably coupled to a threaded portion 114 of a post 112 which is coupled to one of the cutting members 104, such that rotating the knob 116 clockwise or counterclockwise incrementally changes the position of the cutting guide 106 relative to the body 102. Linear displacements of 2 mm, for example, can be achieved in the directions indicated by the double arrow A and corresponding to the anterior or posterior surfaces of the distal femur 82, when the femoral device is mounted on a resected surface 84 of the distal femur 82, as shown in FIG. 9. Other linear actuators 110 can be used to the same effect with cutting guides 106 defined in cutting members 104, and cutting guides 106 defined directly in the body 102, such as ratchet mechanisms, slide mechanism, guiding slots, etc.

Figure 2:
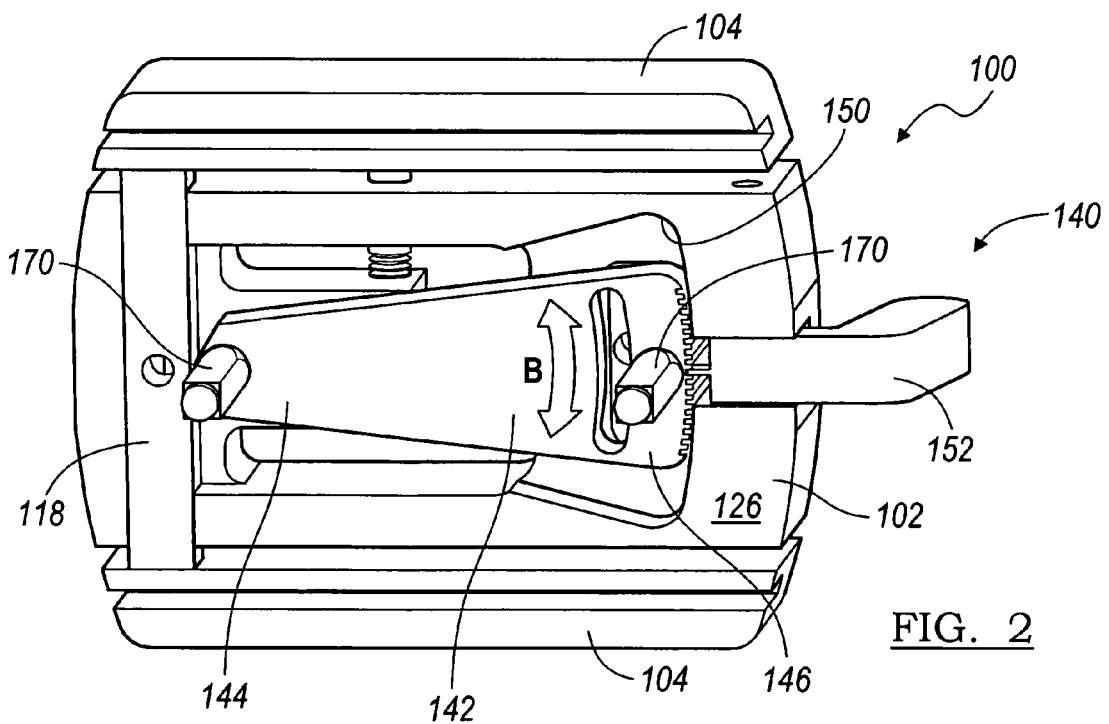
FIG. 2 is a rear isometric view of the femoral adjustment device of FIG. 1.
Figure 3:
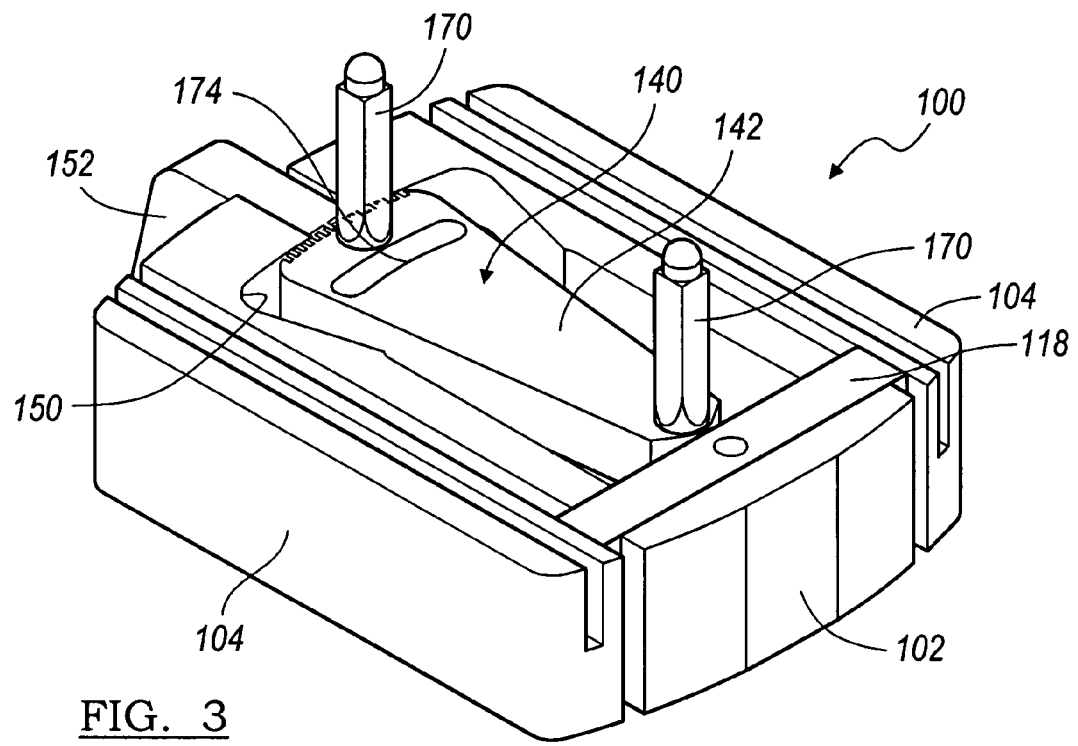
FIG. 3 is another rear isometric view of the femoral adjustment device of FIG. 1.
Figure 8A:
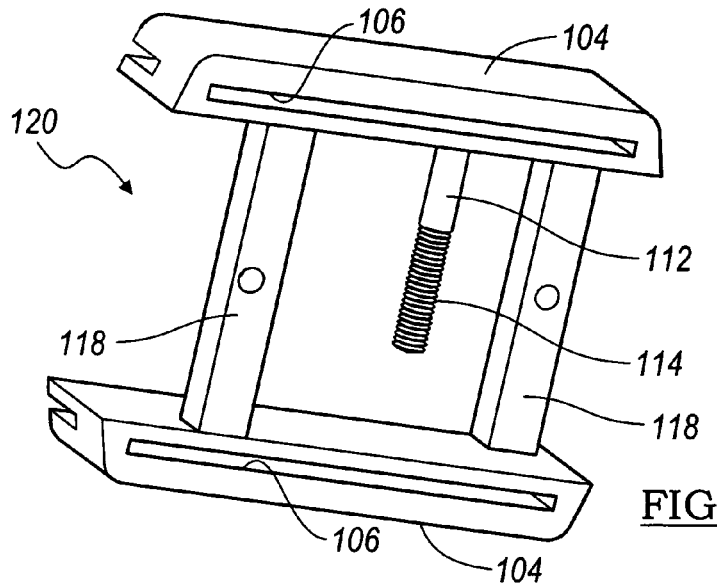
FIGS. 8A-C illustrate various perspective views of cutting members and associated components according to the present teachings.
Figure 8C:
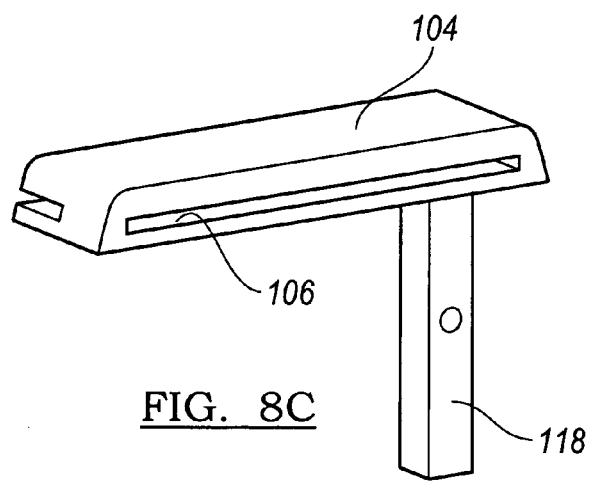
Figure 8B:
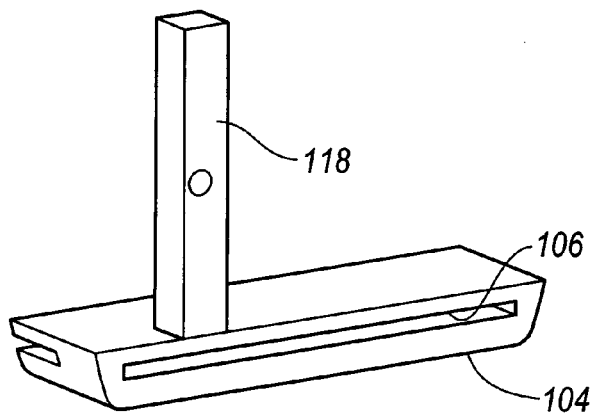

Referring to FIGS. 1-6, and 8A-C, each cutting member 104 can include a column member 118 positioned substantially perpendicular to the cutting member 104. The cutting members 104 and the column members 118 can be interconnected to form a substantially rigid frame 120, as shown in FIG. 8A, in which two cutting members 104 are shown. The frame 120 allows simultaneous linear adjustment of the cutting guides 106 in the A/P direction. The column members 118 can be accommodated in corresponding elongated channels 122 defined in opposite first and second surfaces 124, 126 of the body 102 and shaped to conform to the shape of the column members 118, such that in the assembled femoral adjustment device 100 the column members 118 are flush with the first and second surfaces 124, 126, as can be seen in FIGS. 1-3.

The body 102 can include a cantilever bracket or other support member 130 for supporting the linear adjustment mechanism 108. In particular, the knob 116 can be received between two arms 132 of the support member 130. The post 112 can pass through openings 134 in the arms 132 and body 102. Alternatively, the linear adjustment mechanism 108 can also be secured to the body 102 in any other appropriate manner.

Referring to FIGS. 2, 3, and 7A-E, the femoral adjustment device 100 can include a rotational adjustment mechanism 140 for adjusting a rotational displacement of the cutting guide 106 relative to the resected surface of the femur 82. The rotational adjustment mechanism 140 can include a rotational member 142 having a first end 144 and a second end 146. The first end 144 can be narrower than the second end 146 such that the rotational member 142 can be tapered in width between its first and second ends 114, 146. The first end 144 is pivotably coupled to the body 102 for rotation about an axis C perpendicular to the body 102. The rotational member 142 can be received in a recess 150 defined in the body 102 such that the rotational member 142 is substantially flush with or does not protrude outside of the second surface 126 of the body 102.

Figure 4:
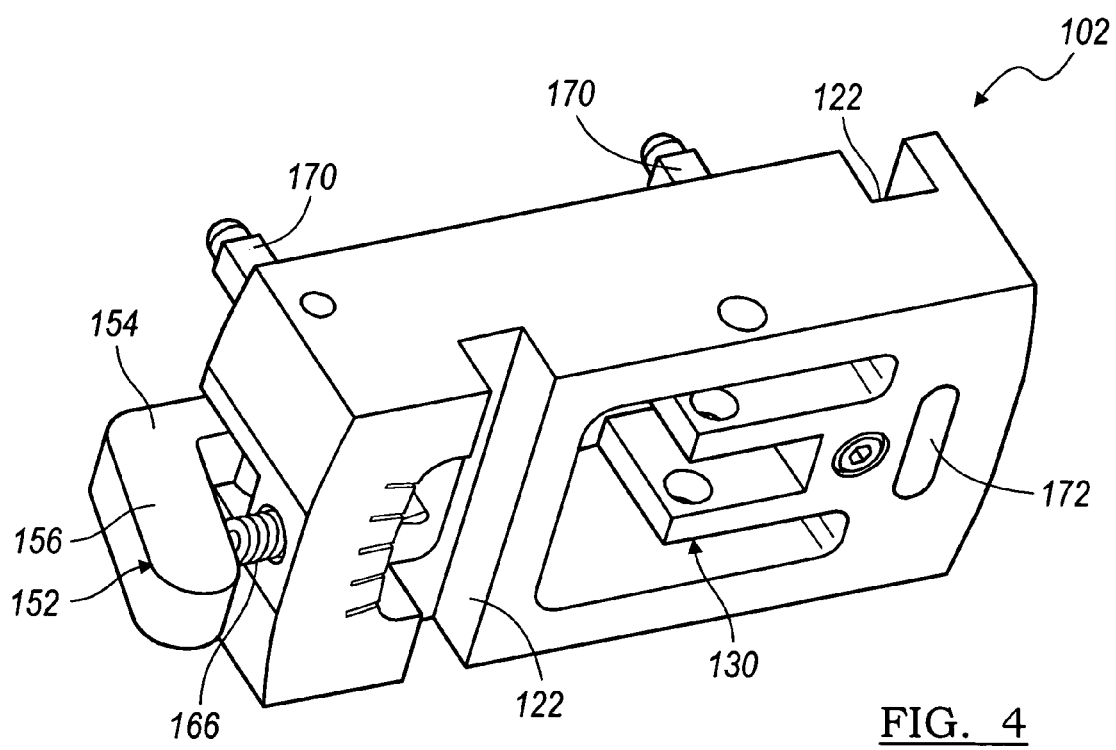
FIG. 4 is a front isometric view of the femoral adjustment device of FIG. 1, shown without the linear adjustment mechanism.
Figure 5:
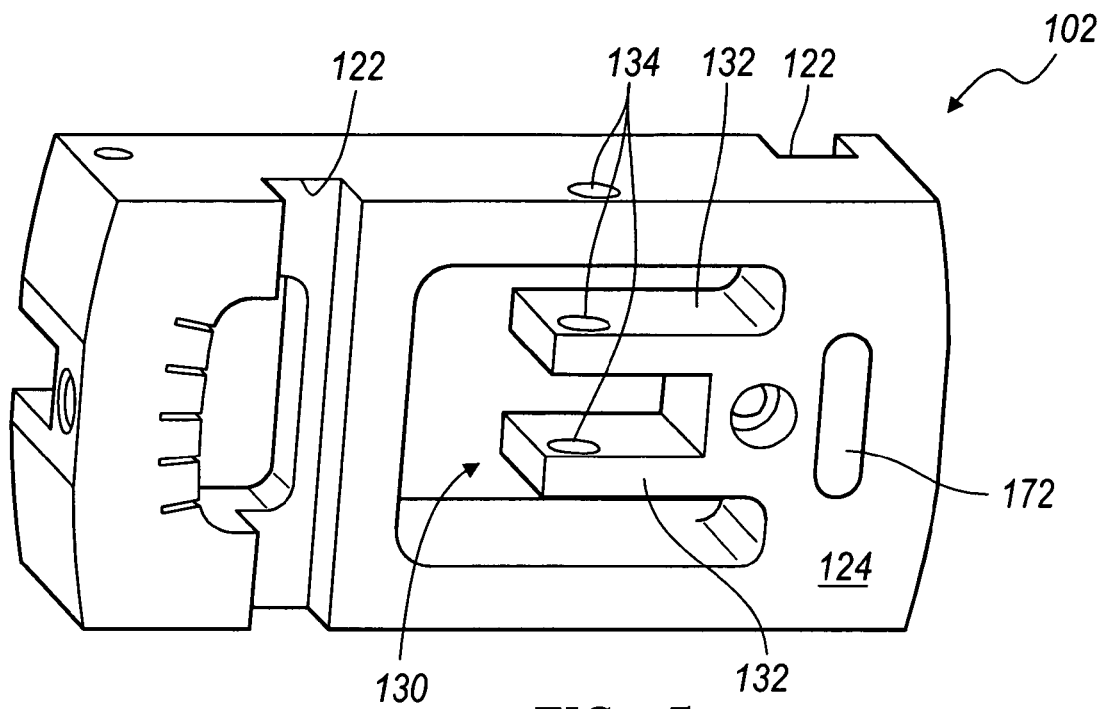
FIG. 5 is a front isometric view of the femoral adjustment device of FIG. 1, shown without a linear and rotational adjustment mechanisms.
Figure 6:
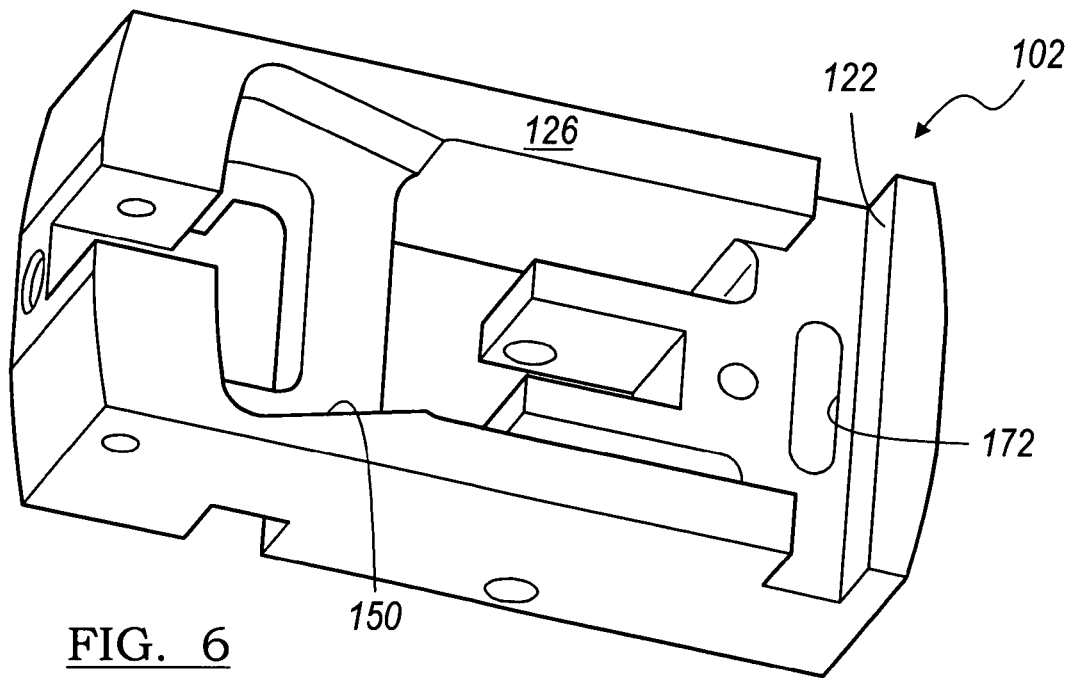
FIG. 6 is a rear isometric view of the femoral adjustment device of FIG. 1, shown without linear and rotational adjustment mechanisms.
Figure 7A:
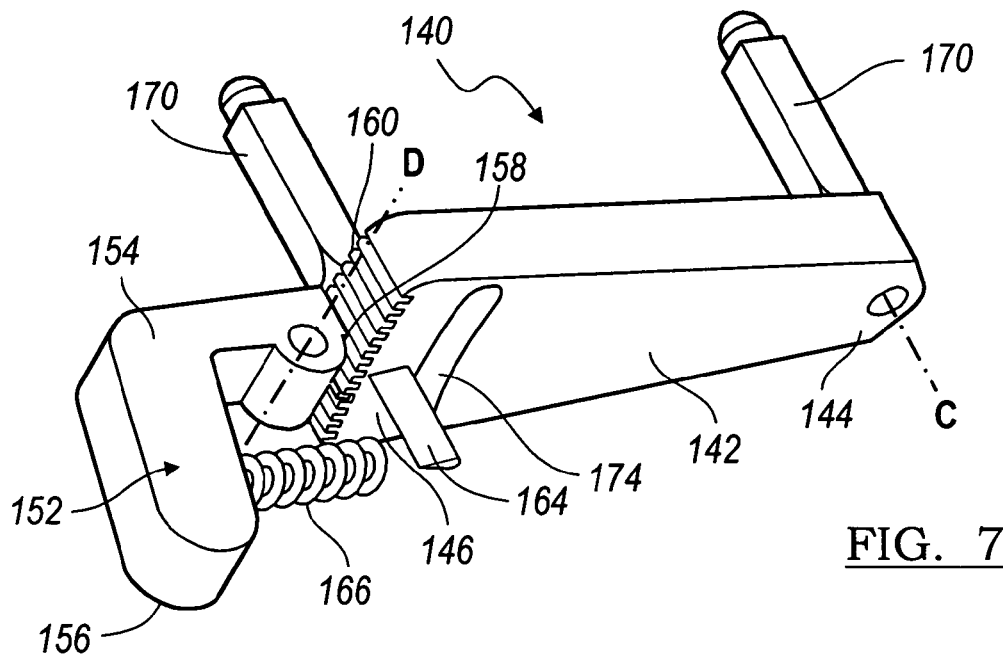
Figure 7B:
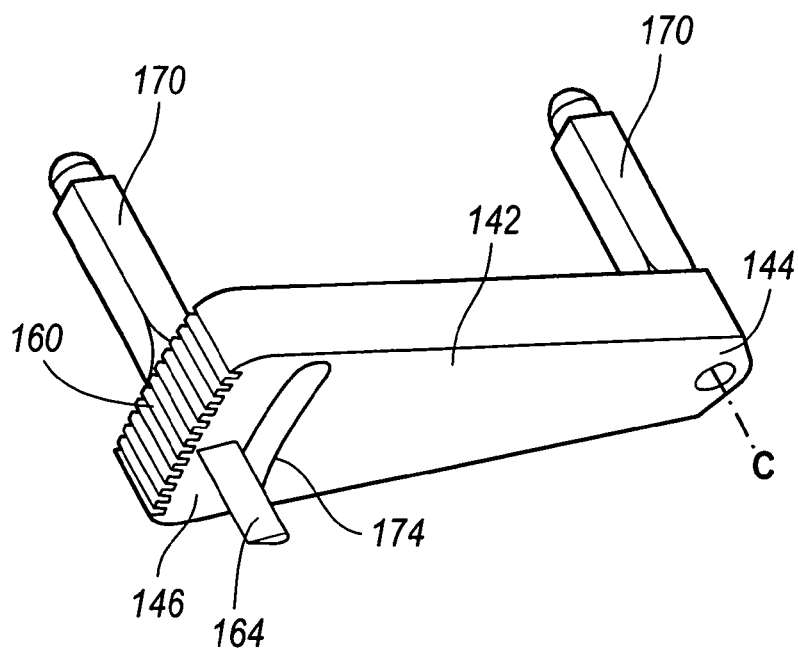

The second end 146 of the rotational member 142 is releasably coupled to the body 102 for permitting rotation between the body 102 and the rotational member 142 about the first end 144 of the rotational member 142, as indicated by the curved double arrow "B" in FIG. 2, by the operation of a lever 152. The lever 152 can be rotationally coupled to the body 102 for rotation about an axis D, shown in FIGS. 7A and 7D. The lever 152 can include first and second portions 154, 156 arranged in an L-shape configuration. The first portion 154 can include a ridge or flange or other engagement member 158 capable of engaging any one of a plurality of slots or grooves or other engagement receivers 160 that are shaped and configured to receive the engagement member 158, such that the rotational member 142 can be held in a plurality of orientations relative to the body 102. These orientations can be indicated on a scale 162 marked on the first surface 124 of the body 102 by an indicator 164 attached to the rotational member 142. The lever 152 is biased in an engagement position that prevents relative rotation between the rotational member 142 and the body 102 by a spring, coil or other biasing member 166. The biasing member 166 is coupled between the main body 102 and the second portion 156 of the lever 152, as shown in FIGS. 4 and 7A. Pressing the lever 152 towards the body 102 compresses the biasing member 166 and causes the lever 152 to rotate, thereby disengaging the engagement member 158 from the engagement receiver 160 and allowing relative rotation between the rotational member 142 and the body about axis C. Because the cutting members 104 are supported on and rotate with the body 102, the direction of the cutting guides 106 relative to the rotational member 142 can be accordingly rotationally adjusted.

The linear adjustment mechanism 108 and the rotational adjustment mechanism 140 together define a two-degree of freedom adjustment mechanism for one or two cutting guides 106 of the femoral adjustment/cutting block device 100.

The rotational member 142 can include one or more bone pins or other bone fasteners 170 for affixing the femoral adjustment device 100 to the resected femoral surface 82. After the cutting guides 106 are adjusted linearly relative to the body 102 and rotationally relative to the rotational member 142, and therefore relative to the bone fasteners 170 and the resected femoral surface 82, one or more holes for attaching other instruments, such as other cutting blocks or four-in-one blocks for anterior or chamfer or other cuts, can be drilled as necessary in the distal femur 82 through the femoral adjustment device 100 using elongated slot 172 in the body 102 (shown in FIG. 1, for example) and elongated curved slot 174 (shown in FIG. 3, for example) in the rotational member 142 for guidance. In this respect, the femoral adjustment device 100, and in particular the slots 172, 174, can operate as a drilling guide for guiding the drilling at least one hole in the distal femur 82.

The femoral adjustment device 100 can be used in knee procedures to balance the flexion gap before various femoral cuts are made for inserting a knee implant. As known in the art, too small flexion gap can result in loss of motion, while too large flexion gap can result in instability. The flexion gap can be measured by placing one or more spacer blocks 180 of increasing thickness on the resected tibia 80 in the flexion gap, as shown in FIG. 9. The spacer block 180 can be stepped, having greater thickness anteriorly. In one exemplary surgical procedure, the tibia 80 and the distal femur 82 are first resected and an extension gap is measured using one or more spacer blocks 180. The distal femur 82 can be sized using a separate A/P sizer, as known in the art. Alternatively, the femoral adjustment device 100 can be provided with sizer stylus 190 movably supported on the body 102, as illustrated in FIG. 1A, such that the femoral adjustment device 100 can also be used for sizing. The stylus 190 can move over the anterior surface of the distal femur 82, by rotation and/or displacement relative to the body 102, such that the femoral size can be determined at the greatest distance from the posterior surface and measured by reading indicia marked on a portion of the body 102, for example. The distal femur 82 and tibia 80 can be moved to the 90-degree flexion position, the femoral adjustment device 100 can then be placed on the resected surface 84 of the distal femur 82 in flexion, and the spacer block 180 inserted in the flexion gap, as shown in FIG. 9. Linear adjustments in the A/P (antero-posterior) direction as well as rotational adjustments can be made as described above using the linear and rotational adjustment mechanisms 108, 140, respectively, until the flexion gap is balanced and matched with the extension gap, and the medial and lateral ligaments of the knee joint are appropriately tensioned. For example, if the medial and lateral ligaments are equally too lax, linear adjustment is made to reduce the flexion gap and move the cutting guides 106 in the A/P direction closer to the body. If the medial and lateral ligaments are equally too taut, linear adjustment can be made to increase the flexion gap and move the cutting guides 106 in the A/P direction away from the body 102. If the medial and lateral ligaments are unequally tensioned, rotational adjustments can be made relative to the longitudinal axis E of the distal femur 82 (substantially perpendicularly to the resected surface 84 of the distal femur 82), until the medial and lateral ligaments are equally tensioned, resulting in a balanced flexion gap. A posterior cut or at least one cut can then be performed through one of the cutting guides 106, as appropriate for the right or left knee.

It will be appreciated that the femoral adjustment device 100 can be used to make posterior, anterior, chamfer or other cuts in either knee after balancing the flexion gap of the particular knee, and as determined by the operating surgeon. Further, it will be appreciated that the femoral adjustment device 100 is also a cutting block device that can be movably attached to the distal femur 82. The femoral adjustment or cutting block device 100 includes an adjustment mechanism (108 and 140) operable to provide adjustment in two degrees of freedom for balancing the flexion gap. The two-degrees-of-freedom adjustments include a linear adjustment and a rotational adjustment. In posterior stabilized knee arthroplasty, for example, the linear adjustment can be in the A/P direction, and the rotational adjustment can be about the longitudinal axis E of the distal femur 82, as shown in FIG. 9. The femoral adjustment device 100 can be used to guide drilling holes into the distal femur 82 for properly attaching other cutting guides after a posterior or other cut is made and the femoral adjustment device 100 is removed. The femoral adjustment device or cutting block device 100 can also be used for A/P sizing using the stylus 190, as shown in FIG. 1A.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A femoral adjustment device to balance a flexion gap, the device comprising:
   a body attachable to a distal femur, the body including a first elongated channel along a first axis;
   a frame movably coupled to the body, the frame including a first column member slidably received in the first channel and an elongated first cutting member substantially perpendicular to the first axis, the first cutting member including an elongated a first cutting guide substantially perpendicular to the first axis; and
   an adjustment mechanism operable to balance the flexion gap, wherein upon balancing the flexion gap, the first cutting guide is operable to guide at least one cut in the distal femur, the adjustment mechanism including:
   a linear adjustment mechanism operable to adjust a linear displacement of the cutting guide relative to the distal femur in a direction parallel to the first axis, the linear adjustment mechanism including a post substantially parallel to the first axis and a knob threadably connected to the post, the post coupled to the first cutting member such that rotating the knob incrementally moves the first cutting guide along the first axis relative to the body; and
   a rotational adjustment mechanism operable to adjust a rotational displacement of the first cutting guide relative to the body,
   wherein the rotational adjustment mechanism comprises a rotational member, the rotational member having first and second ends and a width tapering from the second end to the first end, the rotational member received in a recess of the body, the rotational member pivotably coupled to the body at the first end about a second axis substantially perpendicular to the body and to the first cutting guide, the rotational member releasably coupled to the body at the second end for permitting relative rotation between the body and the rotational member.

2. The device of claim 1, wherein the rotational member comprises at least one bone fastener for attaching the device to the distal femur.

3. The device of claim 1, further comprising an L-shaped lever rotationally coupled to the body for rotation about a third axis substantially parallel to the first axis, the lever engageable with the rotational member and movable from a first position that prevents rotation of the rotational member to a second position that permits rotation of the rotational member, the lever biased in the first position by a spring member.

4. The device of claim 3, wherein the frame includes a second cutting member for selective placement in relation to the distal femur of a left knee or a right knee.

5. The device of claim 4, wherein the first and second cutting members are connected for simultaneous linear motion relative to the body on opposite sides of the body.

6. A method for balancing a flexion gap in a knee procedure, the method comprising:
   attaching a femoral adjustment device to a distal femur, the femoral adjustment device having a body and a cutting member with an elongated cutting guide slidably connected to the body along a first axis substantially perpendicular to the cutting guide;
   selectively adjusting a linear distance between the cutting guide and the body along the first axis by rotating a knob threadably connected to a post coupled to the body and the cutting member, the post substantially perpendicular to the cutting guide and substantially parallel to the first axis;
   selectively adjusting an orientation of the cutting guide relative to the body by rotating a rotational member, the rotational member pivotably coupled to the body at a first end and releasably connected to the body at a second end, the rotational member received in a recess of the body;
   balancing a flexion gap relative to the distal femur by selectively adjusting the linear distance and orientation of the cutting guide; and
   guiding a cut.

7. The method of claim 6, further comprising:
   inserting a spacer block in the flexion gap; and
   measuring the flexion gap.

8. The method of claim 6, further comprising matching the flexion gap to an extension gap.

9. The method of claim 6, further comprising sizing the distal femur with a sizer stylus movably coupled to the body of the femoral adjustment device.

10. The method of claim 9, further comprising affixing the rotational member to the distal femur by at least one bone fastener.

11. A femoral adjustment device to balance a flexion gap, the device comprising:
   a body attachable to a distal femur, the body including a first elongated channel along a first axis and a drilling slot elongated in the direction of the first axis;
   a frame including a first column member slidably received in the first channel; and
   an adjustment mechanism operable to balance the flexion gap, the adjustment mechanism including:
   a linear adjustment mechanism operable to adjust a linear displacement of the body relative to the distal femur in a direction substantially parallel to the first axis, the linear adjustment mechanism including a post substantially parallel to the first axis and a knob threadably connected to the post, the post coupled to the frame such that rotating the knob incrementally moves the frame along the first axis relative to the body;

and a rotational adjustment mechanism operable to adjust a rotational displacement of the body relative to the distal femur, the rotational adjustment mechanism including a rotational member rotatable relative to the body, the rotational member having an elongated curved slot communicating with the drilling slot of the body for guiding a drill, wherein the rotational member is pivotably coupled to the body at a first end and releasably connected to the body at a second end, the rotational member received in a recess of the body.

12. A femoral adjustment device to balance a flexion gap, the device comprising:

a body attachable to a distal femur, the body including an elongated channel along a first axis and a drilling slot elongated in the direction of the first axis;

a frame including a first column member slidably received in the channel and a cutting member substantially perpendicular to the first axis, the cutting member including a cutting guide substantially perpendicular to the first axis; and an adjustment mechanism operable to balance the flexion gap, wherein upon balancing the flexion gap, the cutting guide is operable to guide at least one cut in the distal femur, the adjustment mechanism including:

a linear adjustment mechanism operable to adjust a linear displacement of the cutting guide relative to the distal femur in a direction parallel to the first axis, the linear adjustment mechanism including a post substantially parallel to the first axis and a knob threadably connected to the post, the post coupled to the cutting member such that rotating the knob incrementally moves the cutting guide along the first axis relative to the body;

and a rotational adjustment mechanism operable to adjust a rotational displacement of the cutting guide relative to the distal femur, the rotational adjustment mechanism including a rotational member rotatable relative to the body, the rotational member having an elongated curved slot communicating with the drilling slot of the body for guiding a drill, wherein the rotational member is pivotably coupled to the body at a first end and releasably connected to the body at a second end, the rotational member received in a recess of the body.

* * * * *